United States Patent [19]
Buckholtz et al.

[11] 3,997,560
[45] Dec. 14, 1976

[54] PROCESS FOR THE MANUFACTURE OF THIANTHRENE

[75] Inventors: Harry E. Buckholtz, Kenmore; Arun C. Bose, Niagara Falls, both of N.Y.

[73] Assignee: Hooker Chemicals & Plastics Corporation, Niagara Falls, N.Y.

[22] Filed: Nov. 5, 1974

[21] Appl. No.: 521,108

[52] U.S. Cl. ............................................ 260/327 P
[51] Int. Cl.$^2$ ...................................... C07D 339/08
[58] Field of Search ............................... 260/327 P

[56] References Cited
OTHER PUBLICATIONS

Shirley, *Preparation of Organic Intermediates* (N.Y. Wiley 1951) p. 276.
Gilman et al., JACS 78: 2163–2165 (1956).
Cohen et al., J. Chem. Soc. 75: 887–893 (1899).

*Primary Examiner*—Henry R. Jiles
*Assistant Examiner*—C. Jaisle
*Attorney, Agent, or Firm*—Peter F. Casella; William J. Crossetta, Jr.; Arthur S. Cookfair

[57] ABSTRACT

Thianthrene is prepared by adding sulfur monochloride to an excess of benzene in the presence of aluminum chloride, and reacting at a temperature of 60° to 80° C to form thianthrene as an insoluble thianthrene-aluminum chloride complex; separating the complex by filtration, slurrying the complex in an inert organic liquid; treating the slurry with a Lewis base, such as ammonia to free the thianthrene from the complex and recovering a relatively high purity thianthrene product.

16 Claims, No Drawings

PROCESS FOR THE MANUFACTURE OF THIANTHRENE

BACKGROUND OF THE INVENTION

This invention relates to an improved process for the manufacture of thianthrene. The compound thianthrene, $(C_6H_4)_2S_2$ is useful as a chemical intermediate in the preparation of dyestuffs such as thianthrene vat dyes. Since the first preparation of thianthrene by J. Stenhouse in 1869, various processes for its preparation have been proposed and tried on a laboratory scale, with widely varying results. Little, if any, effort has been directed toward the development of a process suitable for commercial manufacture. Insofar as the applicants have ascertained, only one method described in the prior art for the preparation of thianthrene is of any significance (J.A.C.S. Vol 78, 2163–2164, 1956). In this method, sulfur monochloride is reacted with refluxing benzene in the presence of aluminum chloride, and the reaction product treated with iced hydrochloric acid and steam distilled to remove benzene and steam volatile impurities. The aqueous layer is then decanted off, and the residue filtered. The product is warmed with a sodium hydroxide solution, filtered and washed successively with water and ethanol. The residue is refluxed with an excess of glacial acetic acid, cooled, filtered and washed with ethanol to give 86% yield of crude brown thianthrene. The purity of the product may be improved (with a consequent decrease in yield) by additional distillation and recrystallization from glacial acetic acid.

While this laboratory scale method produces thianthrene, many disadvantages prevent its adoption for large scale commercial production.

Sublimation and subsequent condensation of by-product sulfur is a major problem, leading to plugging of pipelines and creation of pressure buildups which are a detriment to sustained operation. Frequent cleaning of the pipelines and the condensing system is a major industrial problem requiring heavy down time. Reactions utilizing less than 5.0/1.0 stoichiometric proportions of benzene to sulfur monochloride produce a semisolid end product whose rheology is not compatible with proper mixing or gravity discharge of the products from the reactors. This method involves numerous unit operations to make pure thianthrene (no data is indicated in the literature on the percent purity of thianthrene attainable). Additional drawbacks to the adaptation of such a method to commercial production include the use of substantial quantities of ethanol (a federally regulated solvent) and extremely corrosive glacial acetic acid. Furthermore the thianthrene produced remains contaminated and occluded with by-product sulfur and diphenyl sulfide.

It is among the principal objects of this invention to provide a process for the production and recovery of thianthrene and thianthrene based products which is direct and simple and which is adaptable to large scale commercial operation. A further object is to provide a method whereby a high purity grade of thianthrene may be produced in high yields. A still further object is to provide a process for the manufacture of thianthrene which is easily adaptable to subsequent processes such as halogenation for the preparation of thianthrene-based end products. Other objects will become apparent to those skilled in the art on consideration of the complete specification and claims.

STATEMENT OF THE INVENTION

We have now developed a process for the manufacture of thianthrene of high purity. In accordance with the process of this invention thianthrene is prepared by adding sulfur monochloride, preferably with stirring, to a stoichiometric excess of benzene in the presence of aluminum chloride and reacting at a temperature of 60° to 80° Celsius. The theoretical reaction is represented by the equation:

Under the conditions of reaction, in the presence of aluminum chloride the thianthrene forms as an insoluble thianthrene-aluminum chloride complex. The complex is then separated by filtration, slurried in an inert organic liquid and treated with ammonia to free the thianthrene from the complex. The addition of the sulfur monochloride is made slowly to prevent excessively brisk evolution of HCl gas. It is important that the sulfur monochloride be added to the benzene rather than the reverse since the addition of benzene to the sulfur monochloride results in the formation of substantial amounts of undesirable polymeric sulfur products. To provide a reaction medium of suitable consistency for agitation and transfer through piping systems and to provide sufficient solvent for by-product sulfur, diphenyl sulfide and reaction impurities it is important that a molar ratio of benzene to sulfur monochloride be maintained at about 5.0 or higher. Higher ratios may be employed with no theoretical upper limit. However, the process of the present invention becomes somewhat less economical when the mole ratio of benzene to sulfur monochloride is greater than about 12.0 due to the necessity of handling excessively large volumes of liquid. The preferred mole ratio of benzene to sulfur monochloride is between about 6.0 and 8.0.

The amount of aluminum chloride present may vary considerably. However, we have found that maximum yields of thianthrene and minimum production of by-product diphenyl sulfide are achieved when aluminum chloride is present in a mole ratio of aluminum chloride:sulfur monochloride of between about 0.4:1 and 1.6:1. At lower ratios the yield of thianthrene is substantially lowered. At higher ratios, the yield of thianthrene is lowered and the production of diphenyl sulfide is substantially increased. The reaction temperature is maintained between about 60° C and 80° C and preferably between about 65° C and 80° C. At temperatures below about 60° C diphenyl sulfide is produced preferentially. An upper limit of 80° C represents the approximate boiling point of benzene at atmospheric conditions. The process is preferably carried out at atmospheric pressure although subatmospheric and superatmospheric conditions may be employed, if desired, with appropriate adjustments in the upper temperature limit.

The off-gases from the reaction vessel are advantageously routed through heated pipelines to prevent the build-up of sulfur deposits herein to a benzene scrubber. The benzene scrubber, which is preferably maintained at about 70° to 75° C, serves to remove sulfur from the off-gases. The gases may then be routed to a condenser, the problem of sulfur condensation in the condenser having been eliminated by the removal of sulfur. Benzene contained in the off gases may be conveniently recovered in the condenser and recycled to the reactor.

Upon completion of the reaction, the reaction vessel is cooled to room temperature and the contents filtered. The filtrate, consisting of benzene and unwanted reaction by-products and impurities is removed and the remaining solids, a thianthrene-aluminum chloride complex, are slurried in an inert organic liquid, such as monochlorotoluene or benzene. Anhydrous ammonia is sparged through the slurry, preferably at a temperature of between about 25° and 65° C to break the insoluble thianthrene-aluminum chloride complex and separate the thianthrene in the soluble phase. During the ammonia addition, the color of the slurry gradually changes from a black to a light tan color, indicating the completion of the separation of thianthrene from the complex. Essentially complete separation, under the conditions shown may generally be accomplished with the addition of between about 0.3 and 0.5 parts by weight of ammonia per part of crude complex. Aluminum chloride and any residual sulfur form insoluble complexes which are then filtered from the solution. The product thianthrene is then recovered by evaporation and crystallization of the liquor with yields in the order of 75 to 80 percent and a purity of 95-99 percent or higher. This high purity thianthrene product in a soluble phase, in an otherwise inert organic solvent offers considerable advantage in the subsequent preparation of thianthrene based end products.

The following examples illustrate our invention but is to be understood that the specific details given in the examples have been chosen for the purpose of illustrations and are not intended to limit our invention. In the examples, unless otherwise indicated, all parts and percentages are by weight and all temperatures are in degrees Celsius.

EXAMPLE 1

Approximately 4080 parts of benzene was charged to a batch type stirred tank reactor together with 921 parts of aluminum chloride. The charge was heated to 60-70° C and while stirring, 710 parts of sulfur monochloride was fed dropwise into the reactor. The proportion of reactants provided a molar ratio of benzene to sulfur monochloride of about 10 and a molar ratio of aluminum chloride to sulfur monochloride of about 1.3 After sulfur monochloride addition, the resultant mix was refluxed for three hours at 75°–80° C, cooled and filtered. A yield of 1272.4 parts of crude thianthrene:AlCl$_3$ complex was obtained.

One hundred parts of the crude thianthrene:AlCl$_3$ product was slurried in 500 parts of monochlorotoluene in a reaction vessel. The monochlorotoluene employed was a mixture of approximately 50% orthochlorotoluene and 50% parachlorotoluene. Anhydrous ammonia was sparged to the slurry with stirring. The rate of addition of ammonia was optimized by first sparging ammonia so that there was ammonia breakthrough in the reaction vessel followed immediately by cutting back of the rate so that there was no apparent bubbling in the reactor. Temperature was gradually increased and the rate of absorption of ammonia by the slurry by the above technique was recorded. It was found that at 60°–62° C, the absorption rate was 0.1628 parts of NH$_3$ per 100 parts of slurry per minute. Increasing the ammonia rate showed bubbling in the reactor since the slurry can absorb ammonia only at a certain rate. The total ammonia thus sparged was 36.2 parts per 100 parts of crude.

The yield of high purity thianthrene (greater than 99.2% pure, melting at 151°–155° C) was 21.07 parts, or 21.07% based on crude thianthrene:AlCl$_3$ complex. The residue was reslurried in 216.4 parts of monochlorotoluene and recovery by similar procedure was 4.82 parts of thianthrene, m.p. 149°–153° C and 97.48% purity. An additional reslurring of the residue in 216.6 part of monochlorotoluene and reaction with ammonia resulted in the recovery of 1.47 parts thianthrene, having a melting point of m.p. 150°–156° C, and a purity of 96.74%.

Thus it was found that a ratio of 1 part to 10 parts of crude to monochlorotoluene resulted in as nearly maximum extraction of thianthrene in the original crude filter cake, producing a net yield of 61.5% thianthrene based on sulfur monochloride as the limiting reactant.

EXAMPLE 2

Part A.

This experiment relates to improvements in yield through optimization of the AlCl$_3$ catalyst.

Following the procedure of Example 1, 624 parts of benzene was charged to a batch type stirred tank reactor along with 90 parts of AlCl$_3$ and reacted with 108 parts of sulfur momnochloride to yield 175.6 parts of crude thianthrene:AlCl$_3$ complex.

The proportion of reactants provided a molar ratio of benzene to sulfur monochloride of 5.77 and a molar ratio of aluminum chloride to sulfur monochloride of about 0.85. In this experiment, the reactor off gases were scrubbed through a benzene tank before routing them to the condenser. The solubility of sulfur in benzene was sufficient to keep the scrubbed gas free from sulfur. A level controller in the benzene scrubber indicated the recycle feed of benzene. When the level was reached, the recycle amount was distilled off the scrubber and fed back to the thianthrene reactor.

Fifty parts of the crude thianthrene:AlCl$_3$ complex was slurried in 500 parts of orthochlorotoluene and by similar ammonolysis treatment as described in Example 1 18.75 of thianthrene was obtained which gave a net yield of 76.2% based on S$_2$Cl$_2$ as the limiting reactant.

EXAMPLE 3.

This experiment relates to recovery of benzene from the liquor from the thianthrene reactor. It has been observed that by optimizing the AlCl$_3$ catalyst, the formation of by-product, diphenyl sulfide, can be suppressed to a negligible extent.

396.3 parts of the liquor from thianthrene reactor of Example 2 was distilled up and over.

At 79° C refluxing started and benzene was taken off. The operation was stopped when the overhead temperature reached 81° C. 369.3 parts benzene was recovered representing 99.5% of of the theoretical amount of unreacted benzene.

$$\text{Recovery} = \frac{369.3}{396.3} \times 100 = 93.18\%$$

Benzene to sulfur monochloride ratio in the original charge was 624:108 = 5.77.

It will be seen that the foregoing description and examples provide a simple and effective method for the production of thianthrene on a commercial scale. The foregoing specification is intended to illustrate the invention with certain preferred embodiments, but it is understood that the details disclosed herein can be modified without departing from the spirit and scope of the invention.

We claim:
1. A process for the manufacture of thianthrene which comprises adding sulfur monochloride to benzene in the presence of aluminum chloride in a molar ratio of benzene:sulfur monochloride of greater than about 5.0:1.0 and reacting at a temperature of about 60° to about 80° Celsius to yield a crude insoluble thianthrene product in the form of a thianthrene-aluminum chloride complex; separating the complex from the reaction medium; and separating thianthrene from the thianthrene-aluminum chloride complex by admixing the complex with an inert organic liquid solvent for thianthrene to form a slurry therewith, and treating the slurry with a Lewis base to free the thianthrene from the complex and dissolving the thianthrene in the organic liquid solvent.

2. A process for the manufacture of thianthrene which comprises adding sulfur monochloride to benzene in the presence of aluminum chloride in a molar ratio of benzene:sulfur monochloride of greater than about 5.0:1.0 and a molar ratio of aluminum chloride:sulfur monochloride of about 0.4:1 to about 1:6.1 and reacting at a temperature of about 60° to about 80° Celsius to yield a crude, insoluble thianthrene product in the form of a thianthrene-aluminum chloride complex; separating the complex from the reaction medium; and separating thianthrene from the thianthrene-aluminum chloride complex by admixing the complex with an inert organic liquid solvent for thianthrene to form a slurry therewith, and treating the slurry with a Lewis base to free the thianthrene from the complex and dissolving the thianthrene in the organic liquid solvent.

3. A process according to claim 2 wherein said Lewis base is ammonia.

4. A process according to claim 3 wherein said slurry is treated with ammonia at a temperature of about 25° to about 65° Celsius.

5. A process according to claim 4 wherein said organic liquid solvent is benzene.

6. A process according to claim 5 wherein thianthrene product is separated from said benzene by evaporation and crystallization.

7. A process according to claim 4 wherein said organic liquid solvent is monochlorotoluene.

8. A process according to claim 7 wherein thianthrene product is separated from said monochlorotoluene by evaporation and crystallization.

9. In a process for the manufacture of thianthrene which comprises adding sulfur monochloride to benzene, in the presence of aluminum chloride, the improvement which comprises providing a molar ratio of benzene: sulfur monochloride of between about 5.0:1 and 12.0:1, and a molar ratio of aluminum chloride: sulfur monochloride of between about 0.4:1 and 1.6:1 reacting at a temperature of between about 65° and 80° Celsius to form a crude, insoluble, thianthrene-aluminum chloride complex; separating said complex; forming a slurry of said complex in monochlorotoluene; contacting said slurry with ammonia in an amount of between about 0.3 and 0.5 parts by weight of ammonia per part of complex, at a temperature of about 25° to about 65° Celsius and separating thianthrene therefrom by solution in monochlorotoluene.

10. The process for the manufacture of thianthrene wherein thianthrene is separated from a thianthrene-aluminum chloride complex by admixing the complex with an inert organic liquid solvent for thianthrene to form a slurry therewith, and treating the slurry with a Lewis base to free the thianthrene from said complex, and dissolving the thianthrene in said organic liquid.

11. The process according to claim 10 wherein said Lewis base is ammonia.

12. The process according to claim 11 wherein said slurry is treated with ammonia at a temperature of from about 25° to about 65° C.

13. The process of claim 12 wherein said organic liquid is benzene.

14. The process of claim 12 wherein thianthrene product is separated from benzene solvent by crystallization.

15. The process of claim 12 wherein said organic liquid is monochlorotoluene.

16. The process according to claim 15 wherein thianthrene product is separated from monochlorotoluene solvent by crystallization.

* * * * *